(12) United States Patent
Chuang et al.

(10) Patent No.: US 10,961,502 B2
(45) Date of Patent: Mar. 30, 2021

(54) METHOD FOR PREPARING COLLAGEN HAVING REGENERATION AND REPAIR EFFECTS FROM WHARTON'S JELLY MESENCHYMAL STEM CELLS

(71) Applicant: P.E. ASIA BIOMEDICINE CO., LTD., Taipei (TW)

(72) Inventors: Pei-Chuan Chuang, Taipei (TW); I-Fu Chen, Taipei (TW)

(73) Assignee: P.E. Asia Biomedicine Co., Ltd., Taipei (TW)

( * ) Notice: Subject to any disclaimer, the term of this patent is extended or adjusted under 35 U.S.C. 154(b) by 323 days.

(21) Appl. No.: 15/918,111

(22) Filed: Mar. 12, 2018

(65) Prior Publication Data
US 2019/0276798 A1 Sep. 12, 2019

(51) Int. Cl.
*C12N 5/073* (2010.01)
*C07K 14/78* (2006.01)
*C12P 21/00* (2006.01)

(52) U.S. Cl.
CPC ............ *C12N 5/0605* (2013.01); *C07K 14/78* (2013.01); *C12P 21/005* (2013.01); *C12N 2500/05* (2013.01); *C12N 2500/12* (2013.01); *C12N 2500/32* (2013.01); *C12N 2500/38* (2013.01); *C12N 2501/115* (2013.01)

(58) Field of Classification Search
CPC .................................................. C12N 5/0605
See application file for complete search history.

(56) References Cited

FOREIGN PATENT DOCUMENTS

| TW | I362393 B1 | 4/2012 | |
|----|------------|--------|---|
| TW | I435881 B | 5/2014 | |
| WO | WO 98/17791 | * 4/1998 | |
| WO | WO-9817791 A1 | * 4/1998 | ............. C12N 15/85 |

OTHER PUBLICATIONS

Gross et al. Extraction of Collagen from Connective Tissue by Neutral Salt Solutions. PNAS. 1954.*
Doyle et al. Cell & Tissue Culture: Laboratory Procedures, 1993.*
Mazor et al. "Mesenchymal stem-cell potential in cartilage repair: an update." Journal of cellular and molecular medicine 18.12 (2014): 2340-2350 (Year: 2014).*
Doyle et al. ("Doyle"; Cell & Tissue Culture: Laboratory Procedures, 1993) (Year: 1993).*
Gross et al. ("Gross"; Extraction of Collagen from Connective Tissue by Neutral Salt Solutions. PNAS. 1954) (Year: 1954).*

* cited by examiner

*Primary Examiner* — James D Schultz
*Assistant Examiner* — Alexander W Nicol
(74) *Attorney, Agent, or Firm* — Rosenberg, Klein & Lee

(57) ABSTRACT

The present invention disclosed a method for preparing of collagen having regeneration and repair effects from Wharton's Jelly mesenchymal stein cells, comprising steps of culturing the Wharton's Jelly mesenchymal stein cells in a first medium for 16 to 24 hours; replacing the first medium with a second medium for culturing the Wharton's Jelly mesenchymal stein cells for 36 to 48 hours; collecting the Wharton's Jelly mesenchymal stein cells and adding a cell lysis solution to lyse the Wharton's Jelly mesenchymal stein cells for 0.5 to 2 hours, adding an inorganic salt solution to the cell lysis solution to obtain a mixing solution for further incubation at 4° C. for 24 to 48 hours; centrifuging the mixing solution and collecting a sediment, dissolving the sediment by a preservation solution to obtain a collage.

2 Claims, 7 Drawing Sheets

METHOD FOR PREPARING COLLAGEN HAVING REGENERATION AND REPAIR EFFECTS FROM WHARTON'S JELLY MESENCHYMAL STEM CELLS

BACKGROUND OF THE INVENTION

Field of the Invention

The present invention relates a method for preparing collagen having regeneration and repair effects from Wharton's Jelly mesenchymal stein cells, especially for a method of promoting collagen production and extraction from the Wharton's Jelly mesenchymal stein cells cultured by a specific method.

Description of Related Art

Collagens are proteins with elasticity which exist in human skins, bones, cartilages, ligaments, blood vessel walls or connective tissues. In addition, collagens are also important for maintaining elasticity of skin, so collagen loss results in skin sagging and wrinkle formation. Currently, collagens can be applied in many industries, including preparation of cosmetic skin care products or medical products.

Nowadays, the major sources of collagen are extracted from animal tissues, e.g. pig skins, fish scales, and internal organs of animals. The Taiwan Patent No. 1435881 (B), issued on 1 May 2014, disclosed a method of separating collagen from porcine lung and a use of the porcine collagen. The method comprises the steps of reacting the pig lungs with a specific extraction solution, hydrolyzing by pepsin, and salting out to obtain a porcine collagen material. The Taiwan Patent No. 1362393 (B), issued on 21 Apr. 2012, disclosed a new process for the preparation of collagen peptide from fish scales, the process comprises the steps of separating fish scales from fish skin, freezing and stiffening the fish scales to obtain a powder sample, hydrolyzing the powder sample and treating the powder sample with peels from citrus fruits to reduce fishy odor and obtain a collagen with citrus scent. However, collagen materials from animal tissues usually have bad smells and a bitter taste, and may induce allergic reaction.

SUMMARY OF THE INVENTION

The present invention discloses a method for preparing collagen having regeneration and repair effects from Wharton's Jelly mesenchymal stein cells (WJMSC cells). The method comprises the steps of: (a) culturing the WJMSC cells in a first medium for 16 to 24 hours; (b) replacing the first medium with a second medium for culturing the WJMSC cells for 36 to 48 hours; (c) collecting the WJMSC cells, adding a lysis solution to lyse the WJMSC cells for 0.5 to 2 hours; (d) adding an inorganic salt solution to the cell lysis solution to obtain a mixing solution, and incubating the mixed solution at 4° C. for 24 to 48 hours; (e) spinning down the mixed solution and collecting a sediment, and dissolving the sediment by a preservation solution to obtain a collagen.

According to an embodiment of the present invention, the first medium comprises human basic fibroblast growth factor.

According to an embodiment of the present invention, the first medium comprises 2 to 8 ng/mL human basic fibroblast growth factor.

According to an embodiment of the present invention, the first medium comprises 4 ng/mL human basic fibroblast growth factor.

According to an embodiment of the present invention, the second medium comprises at least one of human basic fibroblast growth factor, proline and L-ascorbic acid.

According to an embodiment of the present invention, the second medium comprises at least one of 2 to 8 ng/mL human basic fibroblast growth factor, 0.2 to 2 mM proline and 5 to 50 μM L-ascorbic acid.

According to an embodiment of the present invention, the second medium comprises at least one of 4 ng/mL human basic fibroblast growth factor, 0.2 mM proline and 5 to 50 μM L-ascorbic acid.

According to an embodiment of the present invention, the inorganic salt solution is an ammonium sulfate solution or a sodium chloride solution Therefore, the method for preparing collagen from Wharton's Jelly mesenchymal stein cells of the present invention provides a simple method for collagen mass production.

DETAILED DESCRIPTION OF THE PREFERRED EMBODIMENT

Figure 1:
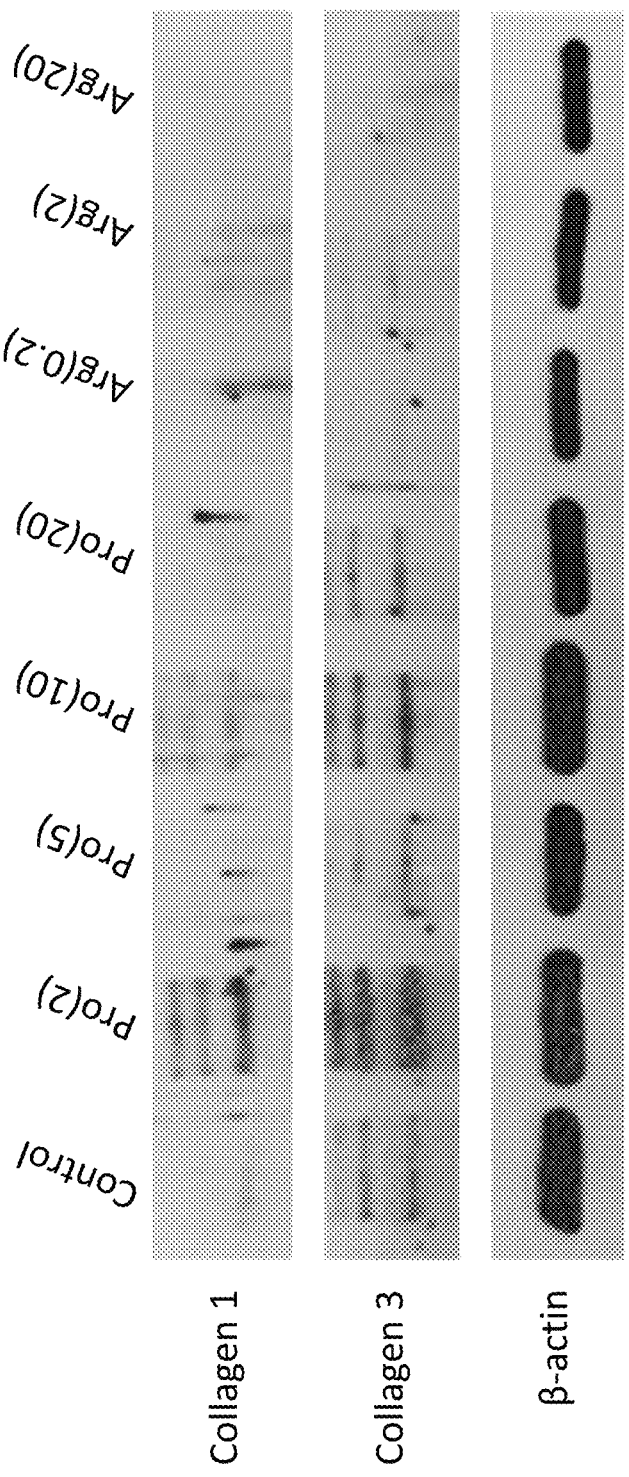
FIG. 1 is an immunoblotting diagram showing effects of amino acids on collagen production of the WJMSC cells.

The present invention relates to a method for preparing collagen from Wharton's Jelly mesenchymal stein cells (WJMSC cells) comprising the steps of: (a) culturing the WJMSC cells in a first medium for 16 to 24 hours; (b) replacing the first medium with a second medium for culturing the WJMSC cells for 36 to 48 hours; (c) collecting the WJMSC cells, adding a lysis solution to lyse the WJMSC cells for 0.5 to 2 hours; (d) adding an inorganic salt solution to the cell lysis solution to obtain a mixed solution, and incubating the mixed solution at 4° C. for 24 to 48 hours; (e) spinning down the mixed solution and collecting a sediment, and dissolving the sediment by a preservation solution to obtain a collagen.

Hereinafter, exemplary embodiments of the present invention will be described in detail with reference to the accompanying drawings.

1. Method for Culturing Wharton's Jelly Mesenchymal Stein Cells (WJMSC Cells)

Wharton's Jelly mesenchymal stein cells (WJMSC cells: BCRC H-WJ001) were cultured in α-MEM medium supplemented with 10% to 20% of fetal bovine serum (FBS) and 2 to 8 ng/mL of human basic fibroblast growth factor (bFGF). In the present invention, the WJMSC cells are incubated in α-MEM medium supplemented with 10% FBS and 4 ng/mL bFGF. In addition, the WJMSC cells are incubated in an incubator with a temperature of 37° C. and 5% carbon dioxide ($CO_2$).

The WJMSC cells were seeded onto culture dishes at a cell density of $5\times10^4$ cells/$cm^2$, and incubated in a first medium of 10% FBS α-MEM medium supplemented with and 4 ng/mL bFGF for 24 hours. After 24 hours, the first medium was removed and the WJMSC cells were washed by 1× phosphate-buffered saline (PBS) for two to three times. The WJMSC cells were then incubated in a second medium for 48 hours. The second medium contains α-MEM medium supplemented with bFGF (ProSpec cat: cyt-218-b), proline (Calbiochem, cat: #5370), arginine (Merck, cat: #1011542) or L-ascorbic acid (Sigma, cat: SI-A8960) as experimental design. After 48 hours, the cells were collected for protein extraction, and expression of type I collagen (abbreviated to "collagen 1") and type III collagen (abbreviated to "collagen 3") was examined.

2. Extraction of Collagen from Wharton's Jelly Mesenchymal Stein Cells (WJMSC Cells)

The cell medium was removed and the cells were washed by 1× PBS for two times. The cells were treated with 10 mM EDTA (ethylenediaminetetraacetic acid)-PBS solution or 0.5 M acetic acid and scraped down at 4° C. to obtain a first mixture. The first mixture was placed into a centrifuge tube for lysing cells by a sonication process. The sonication process comprises sonication at 20 Hz for 15 seconds by an ultrasonicator for three times, and the time interval between each sonication is 30 seconds. After the sonication process, the first mixture was centrifuged at 4° C. at a speed of 2000 rpm for 30 minutes to obtain a protein crud extract.

In addition, a cell lysis buffer can be used for cell protein extraction. The extraction method comprises the steps of removing cell medium, washing the cells by 1×PBS twice, adding RIPA cell lysis buffer containing 10 mM EDTA into the cells and shaking for at least 30 minutes, scraping down the cells to obtain a cells-lysis buffer mixture, placing the cells-lysis buffer mixture into a centrifuge tube, and centrifuging at 4° C. at a speed of 12000 rpm for at least 15 minutes to obtain a protein crud extract.

The protein crud extract was then mixed with 25% saturated ammonium persulfate solution, or mixed with 3M sodium chloride (NaCl) solution for reaction at 4° C. for 24 hours to perform a salting-out process. After 24 hours, the mixed solution was centrifuged at 4° C. at a speed of 3500 g for 30 minutes, and a supernatant was removed to preserve a sediment. The sediment was washed by 1×PBS, and centrifuged at 4° C. at a speed of 3500 g for 30 minutes. The sediment was preserved and dissolved by 0.5 M acetic acid solution to obtain a protein extract. The protein extract was then analyzed by Western blotting assay to detect expression of collagen. All the experiments were repeated at least twice and the results with representative are disclosed.

3. Analysis of Collagen Expression in WJMSC Cells (1) Effects of Proline on Collagen Expression in WJMSC Cells Referring to FIG. 1, effects of different dosages of proline or arginine on collagen expression in WJMSC cells were analyzed. In FIG. 1, "Control" is a control group in which cells does not undergo any treatment, "Pro(2)" is an experimental groups in which cells were treated with 2 mM proline, "Arg(0.2)" is an experimental groups in which cells were treated with 0.2 mM arginine, and so on. As shown in FIG. 1, expression of collagen 1 and collagen 3 are enhanced in cells treated with 2 mM proline. However, the same enhancement effects are not achieved in cells treated with a higher dosage of proline, e.g. 5 mM to 20 mM proline. In addition, expression of collagen 1 and collagen 3 are not enhanced in cells treated with 0.2 mM to 20 mM of arginine.

Figure 2:
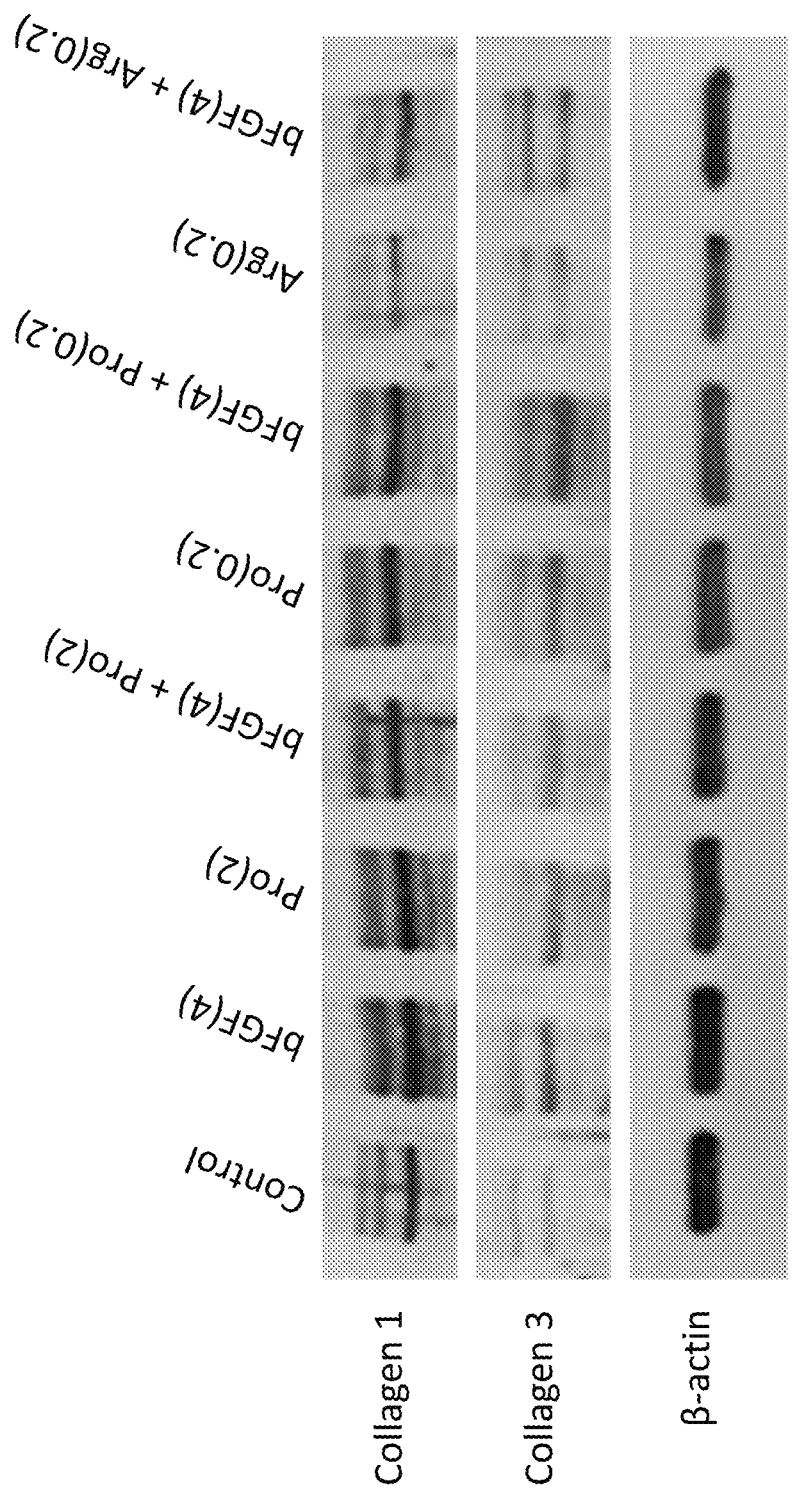
FIG. 2 is an immunoblotting diagram showing effects of growth factors and amino acids on collagen production of the WJMSC cells.

(2) Effects of Human Basic Fibroblast Growth Factor (bFGF) on Collagen Expression in WJMSC Cells Referring to FIG. 2, effects of human basic fibroblast growth factor (bFGF) combined with proline or arginine on collagen expression in WJMSC cells were analyzed. In this embodiment, "bFGF(4)" represents that the WJMSC cells were treated with 4 ng/mL bFGF, "Pro(0.2)" and "Pro(2)" represent that the WJMSC cells were treated with 0.2 mM proline and 2 mM proline respectively, and "Arg(0.2)" represents that the WJMSC cells were treated with 0.2 mM arginine. According to FIG. 2, expression of collagen 1 and collagen 3 are enhanced in cells treated with bFGF, 0.2 mM proline or 2 mM proline. Expression of collagen 1 is not further enhanced in cells treated with bFGF combined with proline. However, compare to cells treated with 4 ng/mL bFGF alone, expression of collagen 3 is further enhanced in cells treated with 4 ng/mL bFGF combined with 0.2 mM proline. Expression of collagen is not enhanced in cells treated with arginine alone or arginine combined with bFGF.

Figure 3A:
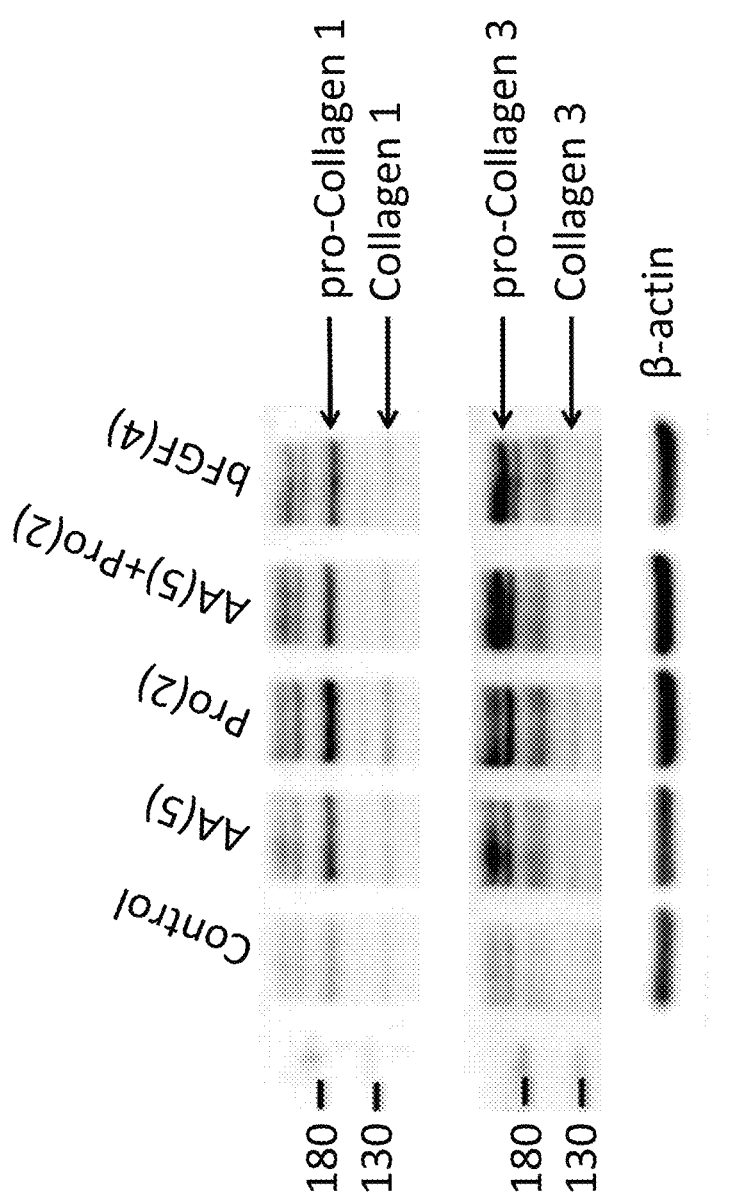
FIG. 3(A) is an immunoblotting diagram showing effects of L-ascorbic acid and amino acids on collagen production of the WJMSC cells.
Figure 3B:
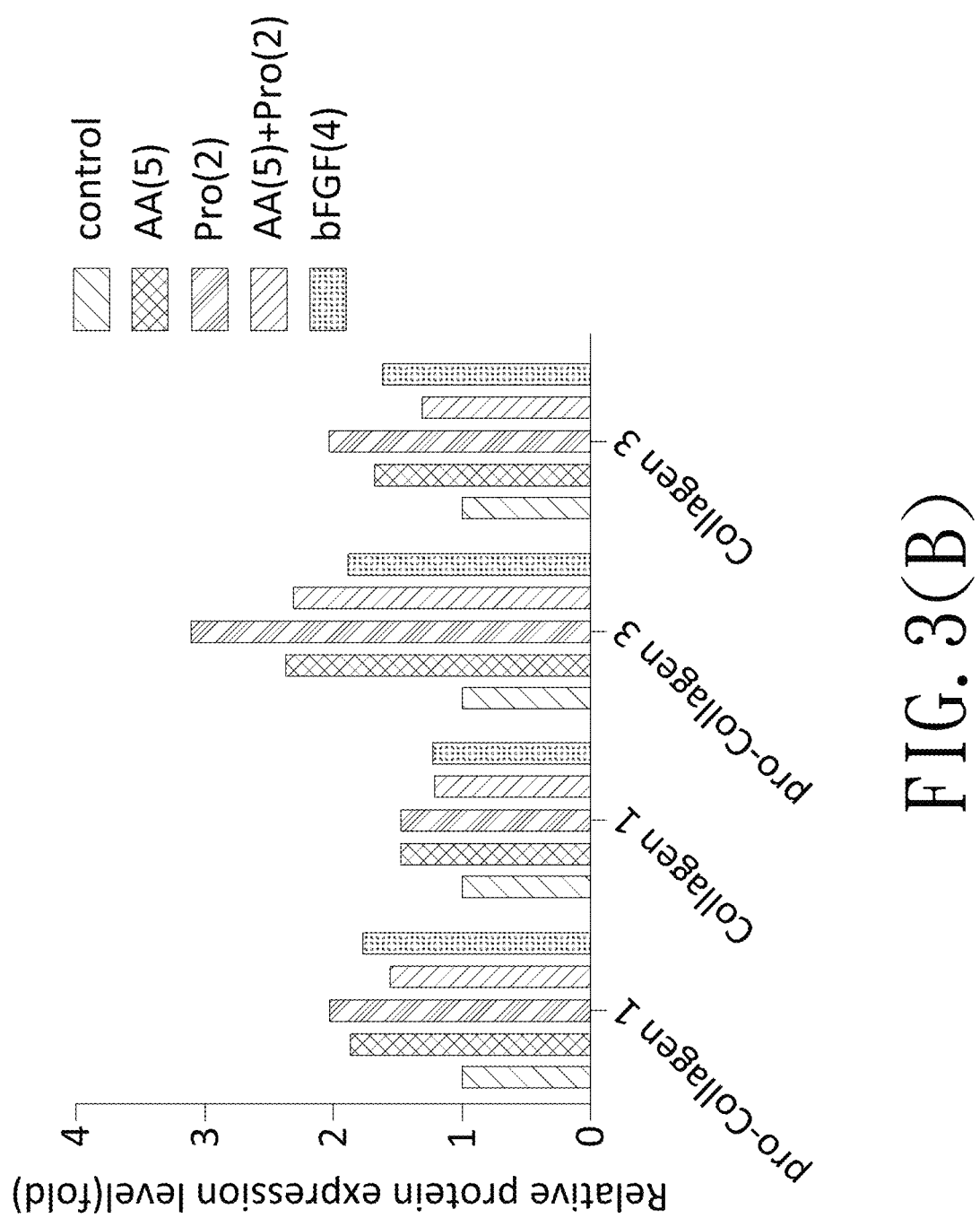
FIG. 3(B) is a quantification bar chart showing effects of L-ascorbic acid and amino acids on collagen production of the WJMSC cells.

(3) Effects of L-Ascorbic Acid And Proline on Collagen Expression in WJMSC Cells FIG. 3(A) is a diagram showing effects of L-ascorbic acid and proline on collagen expression in WJMSC cells. In FIG. 3(A), "AA(5)" represents that WJMSC cells were treated with 5 μM L-ascorbic acid, "Pro(2)" represents that WJMSC cells were treated with 2 mM proline, and "bFGF(4)" represents that the WJMSC cells were treated with 4 ng/mL bFGF. In addition, pro-collagen 1, collagen 1, pro-collage 3 and collagen 3 are marked by arrow signs in FIG. 3(A). According to FIG. 3(A), expression of collagen 1 and collagen 3 are all enhanced in cells treated with 5 μM L-ascorbic acid, 2 mM proline or 4 ng/mL bFGF respectively, but expression of collagens are not further enhanced in cells treated with L-ascorbic acid combined with proline. Referring to FIG. 3(B), the results in FIG. 3(A) are quantified by ImageJ software, the quantification method comprises steps of acquiring a density value of a band of a target in Western blotting and normalizing the density value with a density value of β-actin of the same sample to obtain a normalization value. The normalization value of a tested group was then divided by the normalization value of the control group to obtain a fold change of collage expression. In FIG. 3(B), expression of pro-collagen 1, collagen 1, pro-collagen 3 and collagen 3 are all enhanced in cells treated with 5 μM L-ascorbic acid, 2 mM proline or 4 ng/mL bFGF respectively. In addition, the fold change of pro-collagen 1 and pro-collagen 3 expressions are more obvious.

Figure 4:
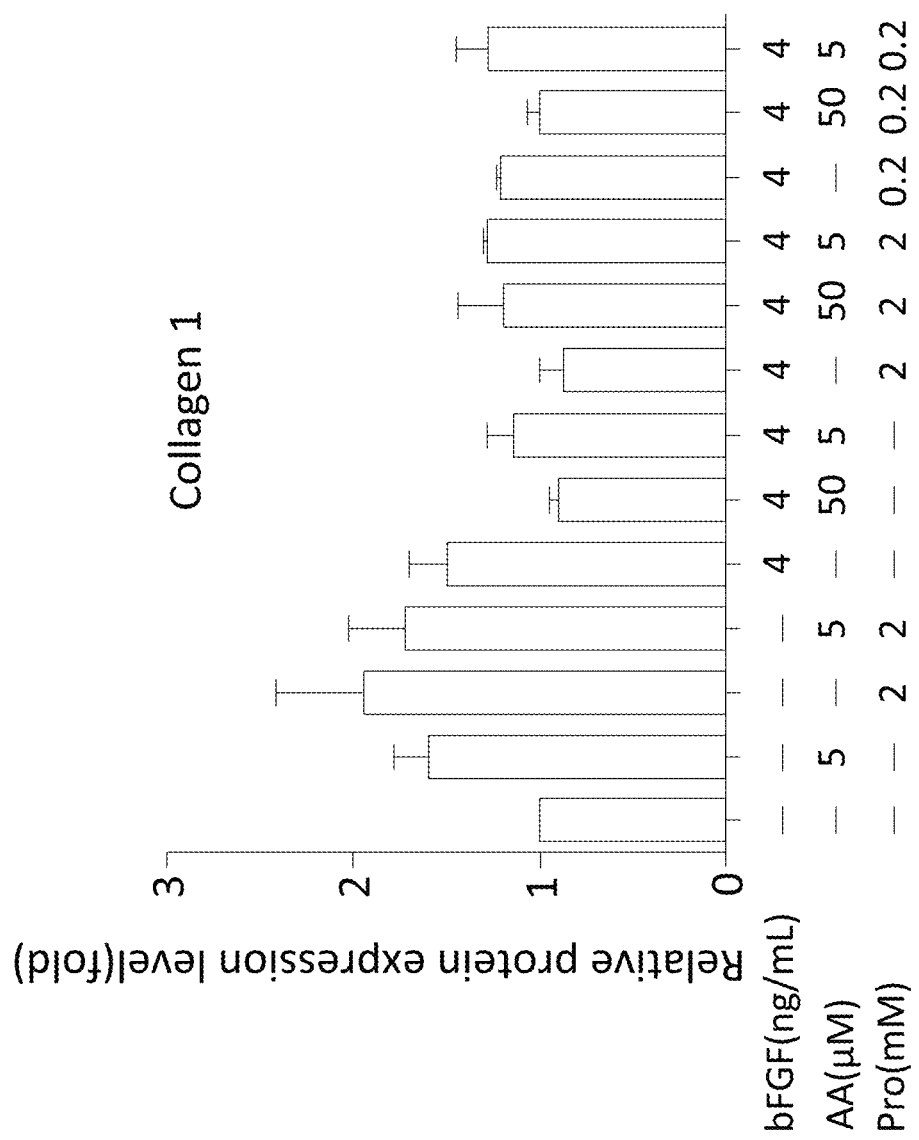
FIG. 4 is a quantification bar chart showing effects of growth factors, L-ascorbic acid and amino acids on type I collagen production of the WJMSC cells.
Figure 5:
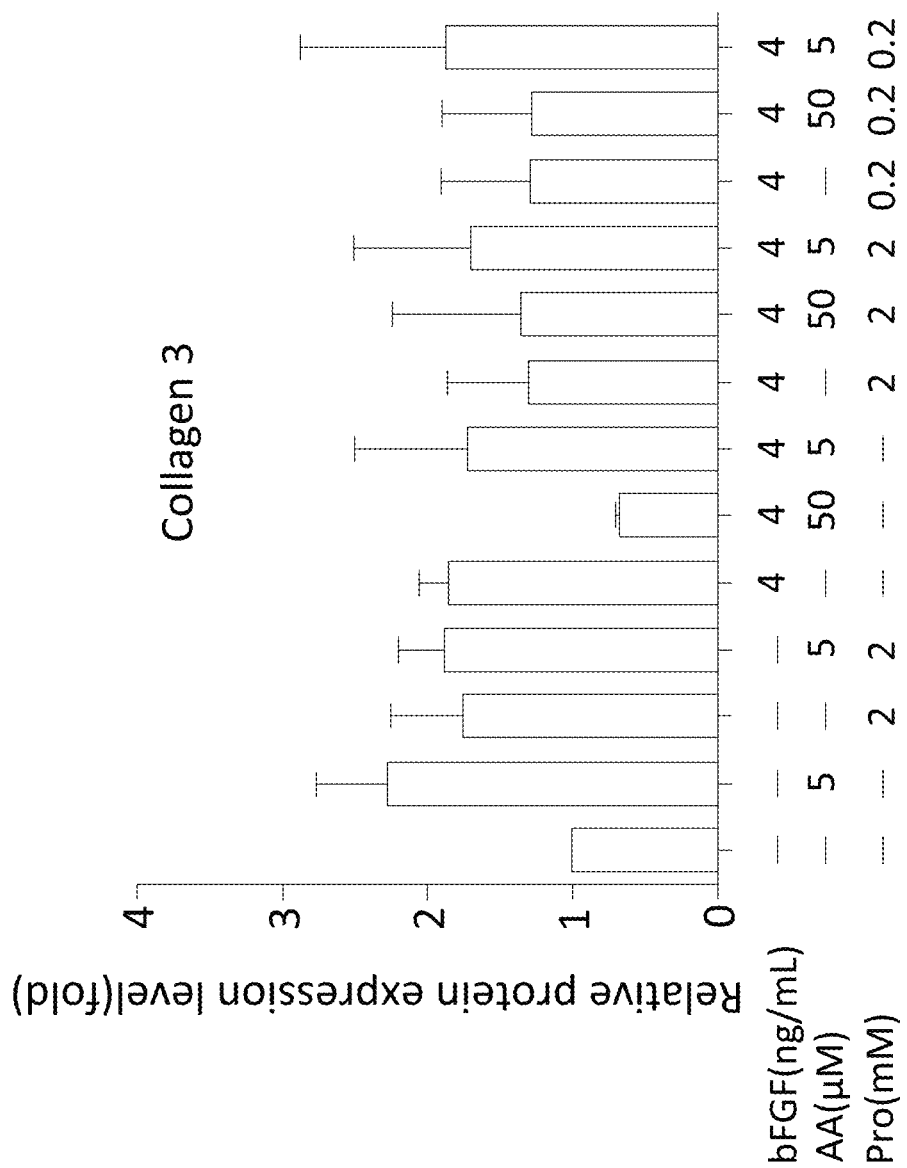
FIG. 5 is a quantification bar chart showing effects of growth factors, L-ascorbic acid and amino acids on type III collagen production of the WJMSC cells.

(4) Effects of bFGF, Proline and L-Ascorbic Acid on Collagen Expression in WJMSC Cells Referring to FIG. 4 and FIG. 5, WJMSC cells were treated with bFGF, proline and L-ascorbic acid, and expression of collagens was analyzed by Western blotting and quantified as described above. According to FIG. 4, expression of collagen 1 is enhanced in cells treated with 5 μM L-ascorbic acid, 2 mM proline and 5 μM L-ascorbic acid combined with 2 mM proline.

Referring to FIG. 5, expression of collagen 3 is not enhanced only in cells treated with 4 ng/mL bFGF combined with 50 μM L-ascorbic acid, and other treatments can enhance expression of collagen 3.

4. Effects of Collagen Extracted from WJMSC Cells on Wound Healing

Human foreskin fibroblasts (HS68) were seed and attached onto a culture dish at a density of $2\times10^4$ cells/cm$^2$ and were incubated in 10% FBS DMEM medium for 24 hours. In control group, an ordinary culture dish without any treatment was used. In collagen group, a collagen-coated culture dish used is prepared by dropping appropriate amount of collagen extracted from WJMSC cells at a concentration of 50 μg/mL on a surface of the culture dish, spreading the collagen evenly, and placing the culture dish into a 37° C. incubator overnight to obtain the collagen-coated culture dish. After the HS68 cells were cultured for 24 hours, the culture medium of HS68 cells was removed and the cells were washed by 1×PBS. A wound was generated on the attached cells, and the wound was observed and photographed at 0, 2, 4, 6, and 20 hours after wound generation by a microscopy. The photographs were analyzed by ImageJ software. The region has no cell on it is considered as a wound size, and a wound healing percentage is calculated by the following formula:

Wound healing percentage (%)=[(wound size at observed time point−wound size at 2 hours after wound generation)/wound size at 2 hours after wound generation]×100%.

The effects of collagen on wound healing are shown in Table 1. In table 1, wound sizes of the two groups are all decreased as time goes by, but wound healing percentage is better in the collagen group than in the control group. After 6 hours of wound generation, wound healing percentage of the control group is 16.1% and wound healing percentage of the collagen group is 38%; after 20 hours of wound generation, wound healing percentage of the control group is 81.7% and wound healing percentage of the collagen group is 100%.

TABLE 1

| Group | Wound size (%) | Wound healing percentage (%) |
|---|---|---|
| Control (2 hr) | 18.7 | — |
| Control (4 hr) | 16.5 | 11.7 |
| Control (6 hr) | 15.7 | 16.1 |
| Control (20 hr) | 3.4 | 81.7 |
| Collagen (2 hr) | 15.2 | — |
| Collagen (4 hr) | 13.3 | 13.0 |
| Collagen (6 hr) | 9.4 | 38.0 |
| Collagen (20 hr) | 0.0 | 100.0 |

Figure 6:
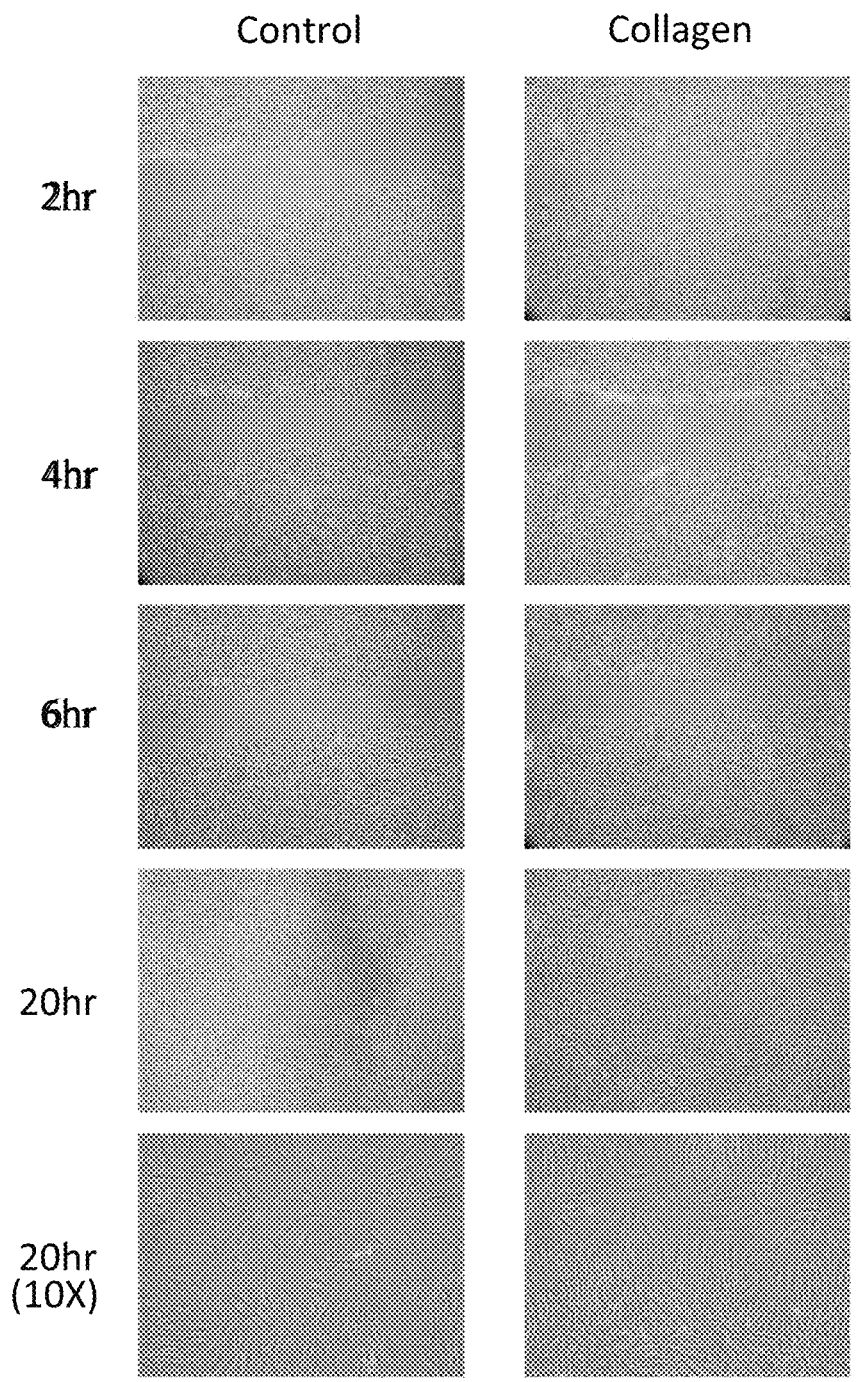
FIG. 6 is a microscopic photograph showing an improvement of wound healing by collagen.

FIG. 6 shows microscopic photographs of the control group and the collagen group in the wound healing experiment. Unlabeled photographs are observed and photographed by 4× objective lens; and photographs labeled "20 hr (10×)" are observed and photographed by 10× objective lens after 20 hours of wound generation. After 4 hours and 6 hours of wound generation, cells were observed on the wound region in the control group, and this phenomenon was more significant in the collagen group. After 20 hours of wound generation, only a small region without cells is observed in the control group, but the wound region in the collagen group is all covered by cells. In addition, in photographs observed by 10× objected lens, cell density was higher in the collagen group than in the control group, suggested that collagen extracted from the WJMSC cells can enhance wound repair.

According to the embodiments above, the present invention has advantages as follows:

1. The present invention disclosed a simple method for mass production of collagen from Wharton's Jelly mesenchymal stein cells cultured by a specific method, and the collagen obtained is human collagen which has low allergy-inducing probability to users.

2. The material used for collagen extraction of the present invention is in vivo cultured cells, so collagen obtained has no fishy odor or bad smell as collagen extracted from animal tissues.

3. The collagen obtained by the present invention has effect on enhancing wound healing, so the present invention can be applied for manufacturing medical or cosmetic compositions for wound repair or wound dressings.

What is claimed is:

1. A method for preparing collagen from Wharton's Jelly mesenchymal stein cells, consisting essentially of:
    (a) culturing Wharton's Jelly mesenchymal stein (WJMS) cells in a first medium for 16 to 24 hours, wherein the first medium comprises 4 ng/mL human basic fibroblast growth factor;
    (b) replacing the first medium with a second medium for culturing the Wharton's Jelly mesenchymal stein cells for 36 to 48 hours, wherein the second medium comprises at least one of 2 to 8 ng/mL human basic fibroblast growth factor, 0.2 to 2 mM proline and 5 to 50 μM L-ascorbic acid;
    (c) collecting the Wharton's Jelly mesenchymal stein cells, adding a cell lysis solution to lyse the Wharton's Jelly mesenchymal stein cells for 0.5 to 2 hours;
    (d) adding an inorganic salt solution to the cell lysis solution to obtain a mixed solution for further incubation at 4° C. for 24 to 48 hours; and
    (e) spinning down the mixed solution, collecting a sediment containing WJMS cells, and dissolving the sediment containing WJMS cells by a preservation solution to obtain a collagen.

2. The method as claimed in claim 1, wherein the inorganic salt solution is an ammonium sulfate solution or a sodium chloride solution.

* * * * *